United States Patent
Peterman, Jr.

(10) Patent No.: US 7,749,446 B2
(45) Date of Patent: Jul. 6, 2010

(54) OPTIMIZED GAS CELL

(76) Inventor: John William Peterman, Jr., 1910 Mayflower Dr., Madison, WI (US) 53562

( * ) Notice: Subject to any disclaimer, the term of this patent is extended or adjusted under 35 U.S.C. 154(b) by 1030 days.

(21) Appl. No.: 10/957,894

(22) Filed: Oct. 2, 2004

(65) Prior Publication Data

US 2006/0073078 A1   Apr. 6, 2006

(51) Int. Cl.
*G01N 33/00* (2006.01)

(52) U.S. Cl. .................................................. 422/83

(58) Field of Classification Search ............ 422/83; 356/246, 432, 440, 437; 250/339.07, 339.12, 250/339.13
See application file for complete search history.

(56) References Cited

U.S. PATENT DOCUMENTS

| | | | | |
|---|---|---|---|---|
| 4,498,182 A | * | 2/1985 | Macklin et al. | 372/62 |
| 4,822,166 A | * | 4/1989 | Rossiter | 356/246 |
| 5,146,283 A | * | 9/1992 | Parnoff et al. | 356/246 |
| 5,220,402 A | * | 6/1993 | Harvey | 356/246 |
| 5,245,405 A | * | 9/1993 | Mitchell et al. | 356/301 |
| 5,508,525 A | * | 4/1996 | Day et al. | 250/339.07 |
| 6,084,668 A | * | 7/2000 | McAndrew et al. | 356/246 |
| 6,114,700 A | * | 9/2000 | Blades | 250/343 |
| 7,064,835 B2 | * | 6/2006 | Riley et al. | 356/437 |

FOREIGN PATENT DOCUMENTS

| | | | | |
|---|---|---|---|---|
| EP | 596605 A1 | * | 5/1994 | |
| GB | 1250477 A | * | 10/1971 | |
| JP | 2000214077 A | * | 8/2000 | |
| JP | 2003014636 A | * | 1/2003 | |

* cited by examiner

*Primary Examiner*—Walter D Griffin
*Assistant Examiner*—Natasha Young
(74) *Attorney, Agent, or Firm*—Stiennon & Stiennon

(57) ABSTRACT

A gas cell used in analytical instrumentation directs the flow of the sample gas to the center of the cell, allowing the outlets to be place on the ends, very near the windows and or mirrors of the cell. This reduces contamination by moving the inlet as far from the ends as possible and improves flow by having the outlets close to the ends of the cell.

11 Claims, 4 Drawing Sheets

OPTIMIZED GAS CELL

CROSS REFERENCES TO RELATED APPLICATIONS

This application claims the benefit of U.S. provisional App. No. 60/499,502, filed Sep. 2, 2003.

STATEMENT AS TO RIGHTS TO INVENTIONS MADE UNDER FEDERALLY SPONSORED RESEARCH AND DEVELOPMENT

Not applicable.

BACKGROUND OF THE INVENTION

This invention relates to sampling methods used in analytical instrumentation.

Gas cells are used in spectroscopy for containing gas samples during analysis. They consist of a containment vessel with optically transparent windows and may include mirrors. In spectroscopy, the absorption of the analyzing beam is proportional to the distance the beam travels through the sample and inversely proportional to the concentration, so gas cells are built with different lengths depending on the types of samples and concentrations that are being analyzed. The distance the beam travels through the sample can be increased through the use of mirrors to reflect the analyzing beam for multiple passes. The length the analyzing beam travels through the sample is referred to as the path length. Gas cells can be used in a continuous flow mode for monitoring or in stop flow mode for static analysis of a sample. Depending on the type of samples being analyzed, they may be heated above ambient temperature in order to reduce condensation. Keeping the optical elements of the cell, the windows and/or mirrors, clean is of utmost importance in order to achieve accurate results. The goal for the gas flow through the cell is to avoid areas where the sampled gas is not readily exchanged. This insures the total path length being analyzed reflects the actual sample being presented to the cell. FIG. 2 shows a typical prior art cell in which two ports for flowing the gas are provided, an inlet port 4 and outlet port 5. The TGC-S10 cell, manufactured by Hayrick Scientific Corporation, Ossining, N.Y., is one example and similar cells are available from other manufacturers. In current practice the inlet and outlet are placed toward the ends of the cell for proper flow. When being used to sample dirty samples such as from a Thermogravimetric Analyzer or pyrolysis, which can contain a number of gases and particulate mater, the position of the inlet near a window or mirror can lead to contamination.

In order to minimize the internal volume of the cell, the cell is sometimes built in the shape of the infrared beam, typically in the shape of two cones placed point to point for use with the focused beam typical for many spectrometers. These cells are heated by placing a band heater in the center of the cell or by a blanket heater covering the entire cell. The typical temperature range is from ambient to 250° C. Cells can be composed of a number of materials including stainless steel, coated aluminum, HASTELLOY®, glass and others. The windows for the cell are composed of a number of materials depending on the spectroscopic wavelength to be used. For Infrared use common materials are KBr, NaCl, KCl, ZeS, among others, while quartz and glass can be used for visible analysis.

SUMMARY OF THE INVENTION

Several problems have been identified with the current designs. 1) In order to have proper flow of gases through the cell the inlet port is placed close to a window or minor on one end of the cell which can lead to contamination or condensation. 2) The practice of heating the center of a cell leads to and results in the windows and/or mirrors being the lowest temperature parts in the cell, which risk condensation occurring on those parts that can most affect spectroscopic results.

To deal with these issues, several innovations have been devised. To improve the flow characteristics, the Split-flow cell was devised. As shown in FIG. 1, the inlet port 4 is placed in the center of the cell and the outlet port 5 is connected to the ends of the cell through the internal vent lines 7A and 7B to the internal vent ports 6A and 6B located on the ends of the internal volume 3. The gas sample flows from the inlet port 4 with one half exiting the internal volume via the internal vent port 6A and the other half via the vent port 6B. This helps in keeping the windows and/or minors clean by having the inlet port 4 placed as far away as possible from the windows 2A and 2B. Since the output flow of the cell is less likely to contaminate, the outlet vents can be placed very close to the windows thus providing better flow. In order to help keep the flow balanced from end to end, the two internal vent ports 6A and 6B are connected together at the centrally located outlet port 5.

The heating of the cell is accomplished by placing heaters on each end as shown in parts 8A and 8B of FIG. 1, insuring the ends where the windows and/or minors are located are keep at the required temperature. This is in contrast with the common practice of placing a single band heater in the center of the cell, thus insuring the windows are at the lowest temperature in the cell leading to the potential of condensation on the least desirable part.

The present invention through the use of split-flow design for introduction of the sample gas and improved heating alleviates the contamination and condensation of the windows and/or mirrors associated with prior designs.

DESCRIPTION OF THE PREFERRED EMBODIMENTS

Figure 1:
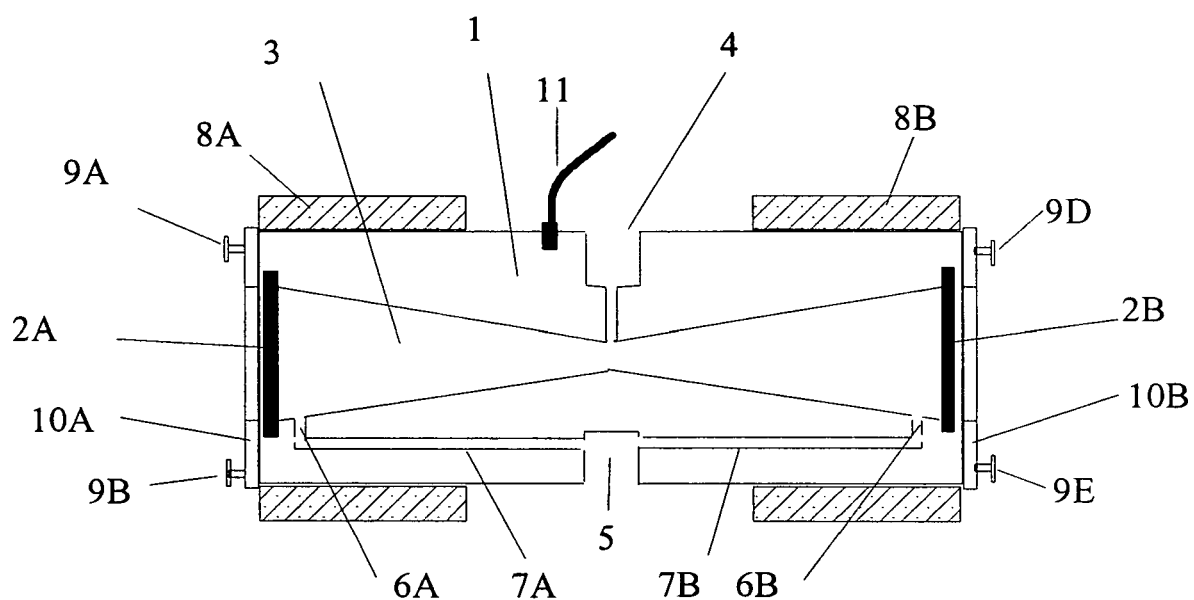
FIG. 1 is a side, cutaway view of a gas cell of the present invention.
Figure 2:
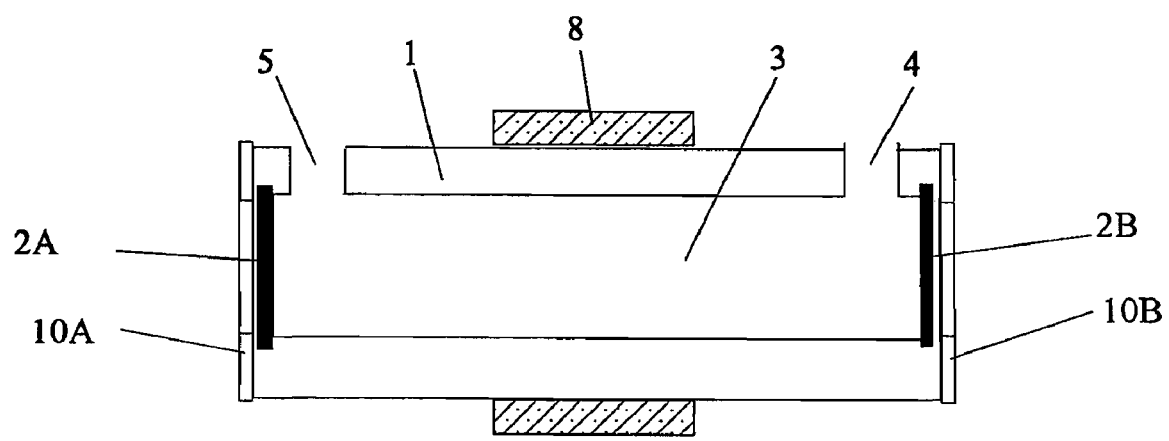
FIG. 2 is a side, cutaway view of a prior art gas cell design.
Figure 4:
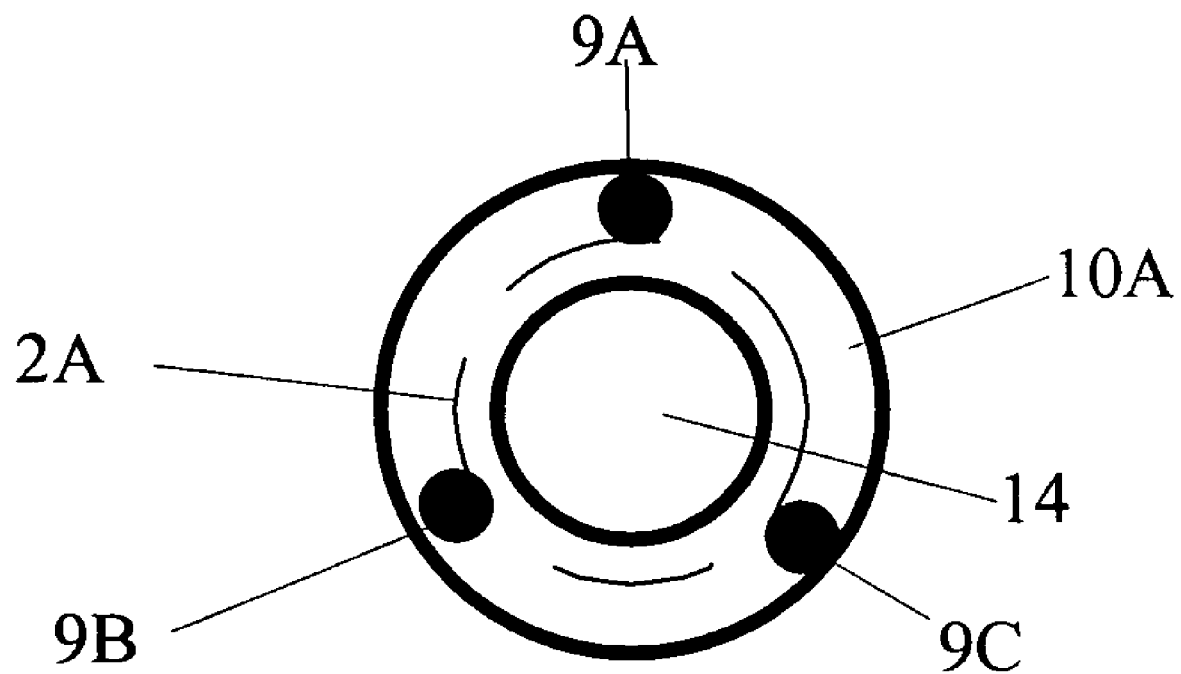
FIG. 4 is a front view of the window holder of the present invention.

The following reference numbers are used in association with the drawings:
1 Cell Body
2A, 2B windows
3 Internal Volume
4 Inlet port
5, 5A, 5B Outlet port
6A, 6B Internal vent ports
7A, 7B Internal vent lines
8, 8A, AB Band heater
9A, 9B, 9C, 9D Window holder screws
10A, 10B Window holder assembly
11 Temperature sensor
12 Analyzing Beam
13a, 13b, 13c Internal Mirrors
14 Analyzing beam hole The preferred embodiment of the system is illustrated in FIG. 1 and FIG. 4. A 100 mm path length version is constructed from a 1.5"×4" aluminum round machined in the double cone shape in the center, in this case to match the center focused beam of a FTIR spectrometer such as the Nexus, available from Thermo Electron, Waltham, Mass. The ends are covered by standard windows such as 2×25 mm KBr available from Spectral Systems, Hopewell Junction, N.Y. and a number of other suppliers. The windows are held in place on the ends of the cell by the window holders 10A and 10B as shown in FIG. 1 and FIG. 4. These consist of a round plate of aluminum with a hole 14 in the center to allow the analyzing beam to pass, held in place with screws 9A, 9B, 9C, 9D, 9E and 9F. The outlet port 5 is connected to the two internal vent ports 6A and 6B via internal vent lines 7A and 7B. This is machined in to the aluminum round by drilling a series of holes, and then plugged on the un-needed ends. This method was done to result in a single piece when finished, but it is not necessary for operation. The venting could also be accomplished through tubing external to the cell, but connection of the two internal vent ports together before connection to a vent is recommend to maintain balanced flow. To provide corrosion resistance, the aluminum is coated by nickel through an electroless process available from Pioneer Metal Finishing, Green Bay, Wis. and other vendors. To heat the cell, two band heaters such as the model STB1J1A1 available from Watlow Electric Manufacturing Co, St. Louis, Mo., are placed on the ends of the cell as shown in FIG. 1, parts 8A and 8B. These band heaters are 120-volt versions, which are connected in parallel for 120-volt operation and in series for use at 240 volts. A K-type thermocouple 11 of FIG. 1 provided temperature feedback to the temperature controller, which powers the band heaters. The cell and heaters are covered in insulation and placed in a box and stand assembly. Sample material is conducted to the cell via heated a ⅛" stainless steel transfer line connected to the inlet port 4. The outlet port 5 is connected to an unheated ⅛" stainless steel line for connection to a vent. The inlet port 4 and the outlet port 5 are threaded for ⅛ NPT and fitted with compression fittings such as SS-2M0-1-2 from Swagelok, Solon, Ohio.

To further improve flow, it is envisioned that additional vent ports could be added on each end of the cell.

Figure 3:
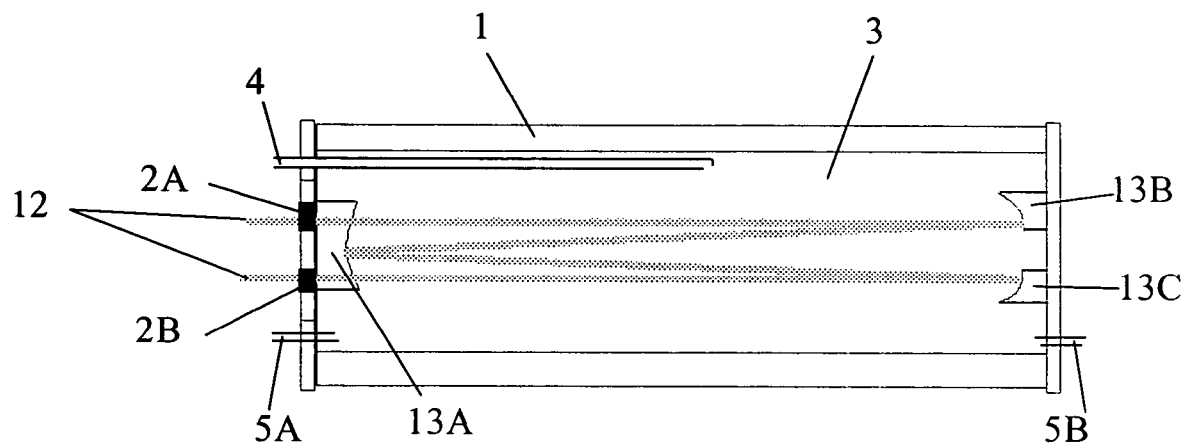
FIG. 3 is a side, cutaway view of a multi path cell with split-flow of the present invention.

The system can also be used with what is referred to as a White cell. Developed by J. White, and described in Long Optical Paths of Large Aperture, 32 J. Optical Society Am. 285 (May 1942). In this type cell, as shown in FIG. 3, the analyzing beam 12 is directed into the cell via the window 2A and then is reflected a selected number of times to increase the path length, by three mirrored surfaces until directed to the other window 2B. As before, the flow for the sample is directed to the center and the outlets are on the ends, in this case via a tube for the inlet port 4 and the outlet ports 5A and 5B.

The cell can be constructed from a variety of materials such as glass, ceramics, stainless steel and other corrosion resistant materials. The method of construction of the cell can be via machining as described, but can also include casting, metal spinning and other common methods of fabrication.

From the preceding discussion, it can be seen that the invention represents a number of advantages over prior versions of gas cells: Reduction in condensation and contamination of the windows and/or mirrors due to locating the inlet for the cell as far as possible from the optical elements; heating on the ends of the cell vs. the center; and improved flow of sample material by placing outlet ports very close to the ends of the cell.

Thus the scope of the invention should be determined by the claims and their legal equivalents, rather then by the examples given.

I claim:

1. A cell for containing a gaseous sample during analysis by absorption spectroscopy, comprising:
    a cell body defining an internal volume; a first window mounted to the cell body: a second window mounted to the cell body, and spaced from the first window with the internal volume therebetween;
    wherein the cell body with internal volume, and the first and second windows define the cell for containing a gaseous sample during analysis by absorption spectrometry;
    portions of the cell body defining a centrally located gas inlet port communicating with the internal volume at a point substantially equidistant from the first window and the second window;
    portions of the cell body defining a first gas outlet port, communicating with the internal volume and positioned closely spaced from the first window; and
    portions of the cell body defining a second gas outlet port communicating with the internal volume and positioned closely spaced from the second window.

2. The cell of claim 1 wherein portions of the cell body define portions of a first cone having a cone base occupied by the first window, and the cell body defining portions of a second cone having a cone base occupied by the second window, and wherein the first cone and the second cone intersect along a common axis to form the internal volume; and wherein the centrally located gas inlet port joins the internal volume where the first cone and second cone intersect.

3. The cell of claim 1 wherein there are a plurality of first gas outlets spaced about the first window, and a plurality of second gas outlets spaced about the second window.

4. The cell of claim 1 wherein the first gas outlet port and the second gas outlet port are internal vent ports which are connected via lines to a single outlet port between the first gas outlet port and the second gas outlet port such that levels of gas flow from the first gas outlet port and the second gas outlet port are substantially equal.

5. The cell of claim 4 wherein portions of the cell body form the lines which connect the first gas outlet port and the second gas outlet port to the single outlet port.

6. The cell of claim 1 wherein the cell body has a first end, containing the first window, and opposite the first end a second end containing the second window, the first end and the second end being aligned along a common axis, and further comprising a first heater positioned at the first end and a second heater positioned at the second end, wherein the first heater and the second heater are spaced apart such that when the first heater and the second heater are activated, the first window and the second window are heated more than the portions of the cell body defining the centrally located gas inlet port substantially equidistant from the first window and the second window.

7. A cell for containing a gaseous sample during analysis by absorption spectroscopy, comprising:
    a cell body defining an internal volume between a first end and a second end;
    wherein the cell body with internal volume between the first end and the second end, define the cell for containing a gaseous sample during analysis by absorption spectrometry;
    a first window mounted to the first end of the cell body:
    a second window mounted to the first end of the cell body spaced from the first window;
    a first mirror mounted to the first end and facing the second end;

a second mirror mounted to the second end, the second mirror facing the first mirror;

a third mirror mounted to the second end, wherein the third mirror faces the first mirror, wherein the first window, the second window, the first minor, the second mirror, and the third mirror are arranged so that an analyzing beam of light can enter the internal volume through the first window, be reflected from the second mirror, the first mirror, and the third mirror, and exit through the second window;

a centrally located gas inlet port connected to the internal volume substantially equidistant between the first minor and the second and third mirrors;

portions of the cell body defining a first gas outlet port, communicating with the internal volume and positioned closely spaced from the first and second windows;

portions of the cell body defining a second gas outlet port communicating with the internal volume and positioned closely spaced from the second and third mirrors; and wherein the gas inlet port, the first gas outlet port, and the second gas outlet port are distinct one from the other.

8. The cell of claim 7 wherein there are a plurality of first gas outlets at the first end, and a plurality of second gas outlets at the second end.

9. The cell of claim 7 wherein the first gas outlet port and the second gas outlet port are internal vent ports which are connected via lines to a single outlet port between the first gas outlet port and the second gas outlet port such that levels of gas flow from the first gas outlet port and the second gas outlet port are substantially equal.

10. The cell of claim 7 further comprising a first heater positioned at the first end and a second heater positioned at the second end, and wherein the first heater and the second heater are spaced apart such that when the first heater and the second heater are activated, the first window, the second window, the first mirror, the second mirror, and the third mirror are heated more than portions of the cell body positioned where the centrally located gas inlet port communicates with the internal volume.

11. A cell for containing a gaseous sample during analysis by absorption spectroscopy, comprising:

a cell body defining an internal volume;

a first window mounted to the cell body:

a second window mounted to the cell body and spaced from the first window with the internal volume therebetween;

wherein the cell body with internal volume, and the first and second windows define the cell for containing a gaseous sample during analysis by absorption spectrometry;

portions of the cell body defining a centrally located gas inlet port communicating with the internal volume at a point substantially equidistant from the first window and the second window;

portions of the cell body defining a first gas outlet port, communicating with the internal volume and positioned closely spaced from the first window;

portions of the cell body defining a second gas outlet port communicating with the internal volume and positioned closely spaced from the second window;

wherein portions of the cell body define portions of a first cone having a cone base occupied by the first window, and wherein the cell body defines portions of a second cone having a cone base occupied by the second window, and wherein the first cone and the second cone intersect along a common axis to form the internal volume; and wherein the centrally located gas inlet port joins the internal volume where the first cone and second cone intersect;

wherein the first gas outlet port and the second gas outlet port are internal vent ports which are connected via lines to a single outlet port between the first gas outlet port and the second gas outlet port such that levels of gas flowing from the first gas outlet port and the second gas outlet port are substantially equal;

wherein portions of the cell body form the lines which connect the first gas outlet port and the second gas outlet port to the single outlet port;

wherein the cell body has a first end, containing the first window, and opposite the first end a second end containing the second window, the first end and the second end being aligned along a common axis, and further comprising a first heater positioned at the first end and a second heater positioned at the second end, wherein the first heater and the second heater are spaced apart such that when the first heater and the second heater are activated, the first window and the second window are heated more than the portions of the cell body defining the centrally located gas inlet port substantially equidistant from the first window and the second window.

* * * * *

UNITED STATES PATENT AND TRADEMARK OFFICE
CERTIFICATE OF CORRECTION

| | | |
|---|---|---|
| PATENT NO. | : 7,749,446 B2 | Page 1 of 1 |
| APPLICATION NO. | : 10/957894 | |
| DATED | : July 6, 2010 | |
| INVENTOR(S) | : John William Peterman, Jr. | |

It is certified that error appears in the above-identified patent and that said Letters Patent is hereby corrected as shown below:

On the Title page, Item [75] of the issued patent, the inventor's address, "Madison" should be -- Middleton --.

Column 1, line 43, "Hayrick Scientific Corporation" should be -- Harrick Scientific Corporation --.

Column 2, line 1, "to a window or minor" should be -- to a window or mirror --.

Column 2, line 16, "the window and/or minors" should be -- the window and/or mirrors --.

Column 5, line 5 and 12, "the first minor" for each occurrence should read -- the first mirror --.

Signed and Sealed this
Nineteenth Day of April, 2011

David J. Kappos
*Director of the United States Patent and Trademark Office*